United States Patent [19]
White

[11] 3,980,768
[45] Sept. 14, 1976

[54] METHOD OF PREPARING A HAIR CARE COMPOSITION

[76] Inventor: Lee Nell White, 17609 Coyle, Detroit, Mich. 48035

[22] Filed: July 26, 1974

[21] Appl. No.: 492,159

[52] U.S. Cl. .................................. 424/70; 424/74
[51] Int. Cl.² ........................................... A61K 7/06
[58] Field of Search ..................... 424/164, 70, 74

[56] References Cited
UNITED STATES PATENTS

| 376,808 | 1/1888 | Pratt | 424/70 X |

FOREIGN PATENTS OR APPLICATIONS

| 434,802 | 12/1911 | France | 424/70 |
| 766,564 | 4/1934 | France | 424/70 |
| 956,840 | 8/1949 | France | 424/70 |
| 971,946 | 8/1950 | France | 424/70 |
| 1,021,806 | 12/1952 | France | 424/70 |
| 570,530 | 12/1957 | Italy | 424/70 |
| 295,839 | 3/1954 | Switzerland | 424/70 |

*Primary Examiner*—Leonard Schenkman
*Assistant Examiner*—Vera C. Clarke
*Attorney, Agent, or Firm*—Irving M. Weiner; Pamela S. Burt

[57] ABSTRACT

A composition for the care of human hair including petrolatum, sulphur, quinine powder, egg yolk, essence of spice, and an alcohol.

4 Claims, No Drawings

METHOD OF PREPARING A HAIR CARE COMPOSITION

The present invention relates to a novel and useful composition which is particularly adapted for the care of human hair. The present invention also relates to methods of preparing and utilizing the aforementioned composition.

BACKGROUND OF THE INVENTION

Heretofore, there have been many attempts to retard the loss of human hair, and to soften and/or thicken human hair, and to improve the growth and manageability of human hair in various different ways. Some of the prior art teachings are briefly discussed hereinbelow in order to set forth the background of the present invention.

U.S. Pat. No. 2,960,442 entitles "HAIRDRESSING METHOD" issued to David R. Schwartz discloses a hair preparation containing nucleic acid as the principal ingredient thereof, and which allegedly improves the managability of hair. The present invention differs from the Schwartz invention in that, amongst other things, the present invention makes no use of nucleic acid as a hair conditioner.

U.S. Pat. No. 3,101,301 entitled "TRANSPARENT WATER AND MINERAL OIL GELS AS HAIR CONDITIONERS" issued to Bernard Siegal and Rita M. Petgrave discloses a clear transparent gel composition and a method of producing the composition. The composition of this patent differs from the present invention in that the invention disclosed in the patent contemplates clear transparent gels comprising substantial quantities of mineral oil and water together with a higher fatty acid alkylolamide, and aliphatic polyglycol ether phosphate, and lanolin alcohols.

U.S. Pat. No. 3,175,949 entitled "EMULSION OF MINERAL OIL, LAURIC DIETHANOLAMIDE, AND WATER" issued to Bernard Segal discloses a clear oil-in-water emulsion and a method of preparing such emulsion, wherein the emulsion comprises mineral oil, water, and linoleic acid diethanol amide. The present invention differs significantly from the patented invention both in composition as well as purpose.

U.S. Pat. No. 3,579,632 entitled "HAIR AND SCALP TREATMENT WITH A PRINCIPALLY SODIUM CHLORIDE THICK VISCOUS AQUEOUS SLURRY" issued to Victor G. Sonnen discloses a hair care preparation designed to increase the manageability of hair, shorten the required drying time, and combat dandruff. The preparation is composed primarily of salt and water, and differs significantly from the present invention both in composition as well as purpose.

U.S. Pat. No. 3,650,280 entitled "COSMETIC TREATMENT OF HAIR WITH THIOUREA OR UREA AND GLYOXAL" issued to David Roberts discloses a non-alkaline composition to beautify hair containing thiourea or urea, glyoxal and an inert cosmetic carrier, and also preferably, benzyl alcohol and diethylene glycol monoethyl ether. The alleged purpose of the disclosed preparation is to elasticize hair, thicken thin hair, and hold thick hair. Although the disclosed invention allegedly provides a means for thickening hair, its composition is completely different from that of the present invention, and also has no application in softening hair as does the present invention.

U.S. Pat. No. 3,728,447 entitled "FATTY ACID LACTYLATES AND GLYCOLATES FOR CONDITIONING HAIR" issued to Lloyd Osipow and Dorothea Marra discloses the use of fatty acid lactylates and fatty acid glycolates in shampoo preparation, rinses, or curling lotions to condition the hair and allegedly to improve its texture, manageability, and curl retention. The disclosed invention differs both in composition and purposes from that of the present invention.

SUMMARY OF THE INVENTION

The present invention provides a composition for the care of human hair comprising petrolatum, sulphur, quinine powder, egg yolks, essence of spice, and at least one alcohol.

The present invention also provides a method for preparing the novel composition for the care of human hair including the steps of combining the sulphur and quinine powder, and mixing the dry resulting mixture with egg yolks. This is followed by the step of mixing the resulting mixture with the petrolatum, and transferring the resulting mixture into a cooking utensil. The mixture in the cooking utensil is then heated, then cooled, then strained, and then returned to the petrolatum container. The alcohol is then added, and this is followed by stirring, and the final step is beating in the addition of essence of spice.

The present invention also provides a method of using the novel composition for the care of human hair, including the steps of first shampooing the hair, and then adding small amounts of the novel preparation to the scalp after the shampooing has been completed.

It is an object of this invention to soften human hair.

It is a further object of this invention to condition human hair.

Other objects and advantages of this new preparation will become apparent to those skilled in the art of hair care as the nature of the composition for the care of human hair and the methods of its preparation and use are revealed in the following disclosure hereinbelow.

DETAILED DESCRIPTION

A preferred method of preparing the novel hair care preparation is hereinafter described.

In the first step of the preparation, approximately two teaspoons of sulphur and approximately one teaspoon of quinine powder are mixed together. This dry mixture is then mixed thoroughly with about two egg yolks.

Next, the sulfur, quinine powder and egg yolk mixture is combined with about one pound of petrolatum, and the resulting mixture is then transferred to a cooking utensil.

The mixture is then cooked slowly, preferably during a total cooking time of about 15 minutes, and is then brought to a rapid, foaming boil at the end of, but within, said 15 minute total cooking time. The pot should then be removed from the stove and the mixture allowed to cool for about 10 minutes.

Next, the cooled mixture is strained three times through a thin cloth, and then returned to the petrolatum container.

About one tablespoon of wood alcohol is then added to the petrolatum composition, and the resulting mixture should then be thoroughly stirred.

Finally, about six drops of oil of cinnamon or cloves should be added to the preparation.

In utilizing this hair care preparation it is preferred that the hair first be shampooed. The subject preparation should then be applied in small quantities to the scalp.

I claim:

1. A method for the preparation of a hair care composition which comprises:
   combining two teaspoons of sulphur and two teaspoons of quinine powder;
   mixing the same with two egg yolks;
   mixing the resulting mixture with one pound of petrolatum;
   transferring the resulting mixture to a cooking utensil;
   heating said mixture;
   cooling said mixture;
   straining said mixture;
   adding one tablespoon of alcohol;
   stirring; and
   adding six drops of oil of cinnamon or cloves.

2. The method according to claim 1 wherein during the heating step the mixture is cooked slowly during a total cooking time of 15 minutes and is then brought to a quick, foaming boil at the end thereof.

3. The method according to claim 1 wherein the mixture is allowed to cool for 10 minutes.

4. The method according to claim 1 wherein the mixture is strained three times through a thin cloth.

* * * * *

UNITED STATES PATENT AND TRADEMARK OFFICE
CERTIFICATE OF CORRECTION

PATENT NO. : 3,980,768
DATED      : September 14, 1976
INVENTOR(S) : Lee Nell White It is certified that error appears in the above-identified patent and that said Letters Patent are hereby corrected as shown below:

Column 3, lines 8-9, after "sulphur and" change "two teaspoons of quinine powder" to --one teaspoon of quinine powder--.

Signed and Sealed this

Twenty-fourth Day of April 1979

[SEAL]

Attest:

RUTH C. MASON
Attesting Officer

DONALD W. BANNER
Commissioner of Patents and Trademarks